United States Patent
Ramakrishnan et al.

(10) Patent No.: US 10,705,069 B2
(45) Date of Patent: Jul. 7, 2020

(54) SYNTHETIC FRACTURED MEDIUM AND METHOD OF FABRICATION

(71) Applicant: SCHLUMBERGER TECHNOLOGY CORPORATION, Sugar Land, TX (US)

(72) Inventors: Terizhandur S. Ramakrishnan, Boxborough, MA (US); Hua Zhang, Chicago, IL (US); Raji Shankar, Cambridge, MA (US); Albert Perez, Jr., Brookfield, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 273 days.

(21) Appl. No.: 15/461,364

(22) Filed: Mar. 16, 2017

(65) Prior Publication Data
US 2017/0269262 A1    Sep. 21, 2017

Related U.S. Application Data

(60) Provisional application No. 62/309,236, filed on Mar. 16, 2016.

(51) Int. Cl.
*C03B 19/06* (2006.01)
*G01N 33/28* (2006.01)

(52) U.S. Cl.
CPC ............ *G01N 33/28* (2013.01); *C03B 19/06* (2013.01)

(58) Field of Classification Search
CPC .............. C03B 19/06; B28B 21/42–50; B28B 21/90–905
USPC .................................................. 264/628–632
See application file for complete search history.

(56) References Cited

U.S. PATENT DOCUMENTS

| | | | | |
|---|---|---|---|---|
| 4,970,035 A | * | 11/1990 | Baarsch | B01D 39/2093 264/317 |
| 6,053,012 A | * | 4/2000 | Itoh | C03B 37/012 65/389 |
| 2009/0205372 A1 | * | 8/2009 | Takekoshi | C03B 11/005 65/61 |
| 2016/0341477 A1 | * | 11/2016 | Golshokooh | B01D 39/201 |

* cited by examiner

*Primary Examiner* — Erin Snelting

(57) ABSTRACT

Consolidated porous media samples and methods for their manufacture are described herein. An assembly has an outer tube having a first softening temperature and a sintered glass construct formed from plurality of beads of multiple sizes. The sintered glass construct defines pores and at least one fracture or channel. The assembly is formed by suspending at least one sheet or wire of dissolvable material in the outer tube, packing beads of different sizes around the sheet or wire, sintering the beads with the sheet or wire located therein at a temperature below the softening temperature of the tube, and dissolving the sheet or wire to generate a sintered construct defining at least one fracture or channel.

14 Claims, 2 Drawing Sheets

SYNTHETIC FRACTURED MEDIUM AND METHOD OF FABRICATION

RELATED APPLICATIONS

This application claims the benefit of U.S. Provisional Application Ser. No. 62/309,236, filed Mar. 16, 2016, which is hereby incorporated by reference herein in its entirety.

TECHNICAL FIELD

The subject disclosure relates to the fabrication of a consolidated porous medium with one or more fractures. The subject disclosure has particular use in enabling analysis and modeling of enhanced oil recovery in fractured systems although it is not limited thereto.

BACKGROUND

In studying the production of hydrocarbons from a rock formation, physical models of the rock formation have been generated. In particular, media constructed with borosilicate glass beads of varying sizes have been utilized. The borosilicate glass beads are sintered and the resulting glass construct is used as a replica of the formation rock. Fluids of matching refractive indices have been introduced into the glass construct, and because the glass construct is translucent or transparent, the flow of fluid may be visualized. In this manner, the flow of hydrocarbons through a formation may be studied. By way of example only, hydrocarbon fluid may be introduced into the glass construct, and then a brine may be introduced under desired pressure in order to study the displacement of the hydrocarbon by the brine in the glass construct.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Illustrative embodiments of the present disclosure are directed to a physical model of an earth formation. The physical model includes a sintered construct with pores. The sintered construct defines at least one fracture and/or channel extending at least partially through the sintered construct. The sintered construct is formed from beads of multiple sizes.

Various embodiments of the present disclosure are directed to a method for generating a physical model of an earth formation. The method includes suspending at least one thin fracture and/or channel-sized chemically-dissolvable material in a hollow structure. The method further includes filling the hollow structure around the thin material with beads of varying sizes. The beads have a softening temperature below the softening temperature of the hollow structure. The method also includes subjecting the filled hollow structure to a temperature at or above the softening temperature of the beads and below the softening temperature of the hollow structure in order to sinter the beads within the hollow structure. Then, the method includes introducing a solvent into the sintered construct in order to dissolve the thin material and define at least one fracture or channel in the sintered construct. When the thin material is a sheet of material, the result of the dissolving of the thin material will be a fracture, and when the thin material is a thin wire, the result will be a channel.

In one embodiment, the hollow structure is a quartz tube which may be rectangular or round in cross section, the beads are borosilicate glass, and the chemically-dissolvable material is a metal, such as copper, zinc or tin. In another embodiment, the hollow structure is a borosilicate glass tube, the beads are soda-lime glass, and the chemically-dissolvable material is a metal sheet or wire.

Additional aspects, embodiments, objects and advantages of the disclosed methods may be understood with reference to the following detailed description taken in conjunction with the provided drawings.

DETAILED DESCRIPTION

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show details in more detail than is necessary, the description taken with the drawings making apparent to those skilled in the art how the several forms of the subject disclosure may be embodied in practice. Furthermore, like reference numbers and designations in the various drawings indicate like elements.

For purposes herein, a "fracture" means a continuous void space defined in a construct of sintered beads, where the continuous void space is at least one hundred times larger than the average pore size defined between the sintered beads in at least two directions (when the fracture is generally planar), and at least twice the average pore size in a third, typically vertical, direction. This forms the "aperture" of the fracture. For nonplanar fractures, the two directions are understood to be locally tangential and the third direction is locally orthogonal to the tangential directions. The coordinates may be generalized curvilinear coordinates.

As will be described below, the surface of the fracture will be defined by a material (e.g., sheet or wire) that survives a softening temperature to which the beads are subjected in order to sinter the beads.

Also, for purposes herein, a "channel" means a continuous void space defined in the construct of sintered beads, where the continuous void space is at least one hundred times larger than the average pore size between sintered beads in one direction, and at least twice the average pore size in second and third directions. In some embodiments, channels are generally substantially cylindrical.

Furthermore, for purposes herein, "softenining temperature" means the temperature at which a material begins to measurably deform. In the case of glass beads, a temperature above the softening temperature will be sufficient to bond the beads to one another.

In one aspect, it will be appreciated that many hydrocarbon reservoirs are located in earth formations that are naturally fractured as a result of variability in rock strength and in situ stress. Variations in strength are generally due to differences in mineralogy, diagenesis, and cementation. During hydrocarbon production, the hydrocarbons within the fractures of carbonate rocks are also preferentially displaced if the matrix does not spontaneously imbibe the injected brine. Study of fractured systems can be important for evaluating efficient methods of hydrocarbon recovery. The embodiments described hereinafter provide physical models of rock formations containing fractures and/or channels, and methods of forming the same.

Figure 1:
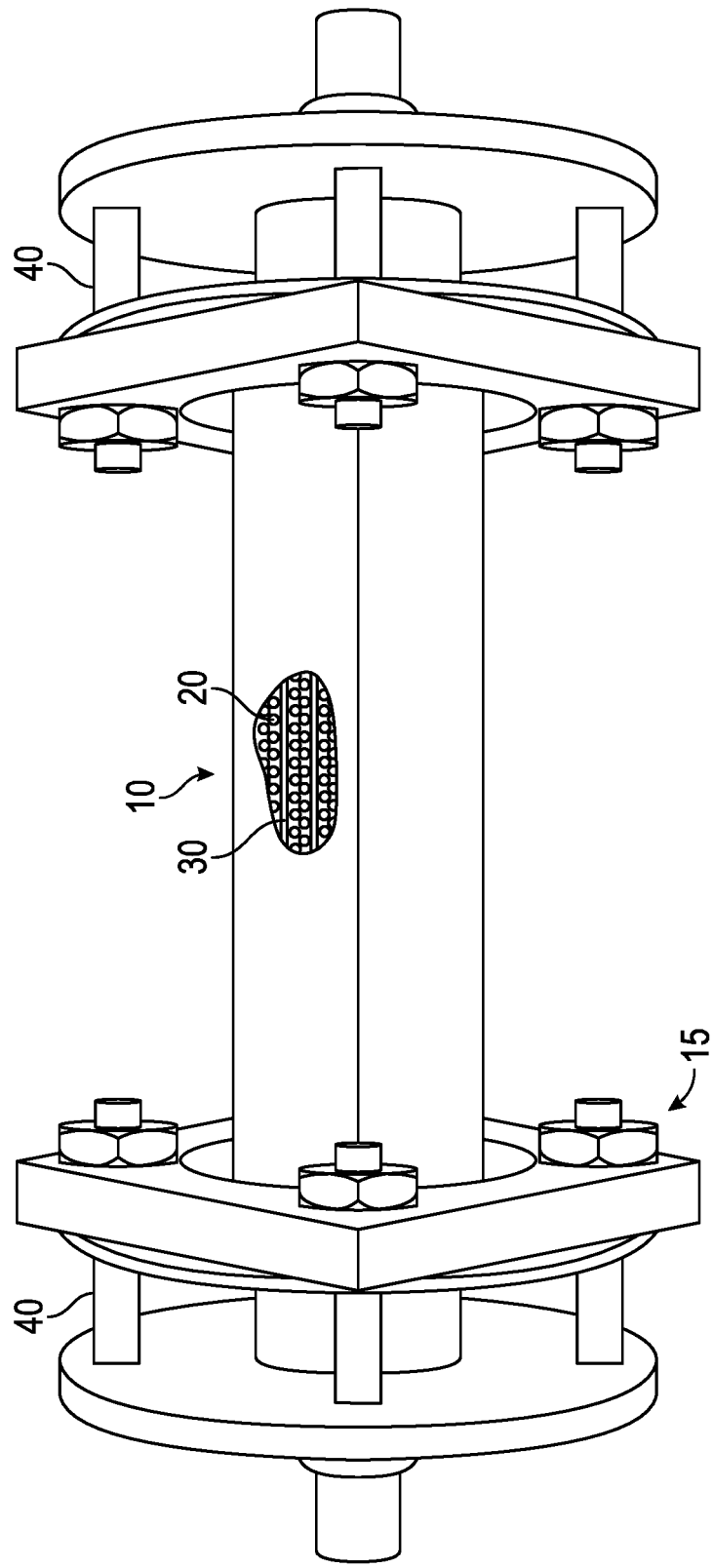
FIG. 1 is diagram of an apparatus for generating a physical model of an earth formation.

As seen in FIG. 1, a quartz tube 10 of desired cross-section (e.g., 12 mm×12 mm) and desired length (e.g., approximately 76 mm) is positioned on a rigid platform 15. Inside the tube 10 are borosilicate glass beads 20 of specified sizes (e.g., 100 micron, 80 micron, 70 micron, and 60 micron) and volume fractions which in one embodiment are randomly packed inside the tube. Running inside the tube is a thin copper sheet 30 of desired thickness (e.g., approximately 0.5 mm) and desired width and length (e.g., 10 mm×76 mm), and the beads 20 are packed inside the tube 10 and about the sheet 30.

In one embodiment, the open end(s) of the tube 10 are closed by high temperature blocks 40 with the beads 20 and sheet 30 in place and the assembly of the blocks 40, tube 10, beads 20 and sheet 30 is placed in a furnace. The furnace temperature which was set to approximately 800° C., and is then slowly (e.g., over a period of at least five, ten or fifteen minutes or more) brought up to the softening temperature for the borosilicate glass beads (e.g., approximately 830° C.) and held thereabouts for a desired amount of time (e.g., 20 minutes) to permit sintering of the beads 20. The assembly is then either removed from the furnace, or the furnace temperature is cooled gradually, resulting in a sintered construct defining numerous pores and that is similar in various respects to consolidated sandstone, except that it contains the copper sheet 30 suspended therein. One or both of blocks 40 are then removed from the assembly, and the sintered construct is soaked in a solvent such as nitric acid or ferric chloride that dissolves the copper sheet but that does not materially impact the sintered construct. The solvent may then be drained into a collector (not shown) and the sintered construct which now defines a fracture where the copper sheet was located may be flushed with a distilled deionized water. After multiple pore volumes of flushing, the fractured sintered construct may be dried (e.g., in vacuum).

A three-dimensional rendering of an elongate fractured sintered construct 100 generated as described above is seen in FIG. 2 and includes a matrix 120 of sintered beads of borosilicate glass defining a fracture 130. The sintered construct 100 has a longitudinal axis 131 as well as a lengthwise dimension between opposed ends 132 and 133. The fracture 130 extends along the entire lengthwise dimension of the sintered construct 100 in the direction of the longitudinal axis 131. It will be appreciated that the fracture 130 is approximately 0.5 mm thick×10 mm wide×76 mm long. It will also be appreciated that the sintered beads form a porous structure with pores of different sizes, but generally of an average size of less than 0.05 mm diameter. Thus, it will be appreciated that the fracture 130 constitutes a non-random space defined in the sintered construct 100 where the width and length of the fracture 130 are at least one hundred times larger than the average pore size defined between sintered beads, and the height of the fracture 130 is at least twice the average pore size.

Figure 2:
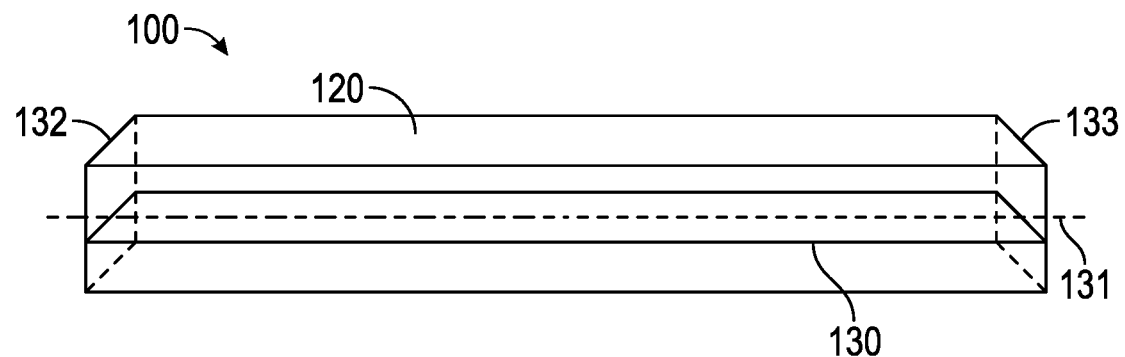
FIG. 2 is a three-dimensional rendering of a physical model of a formation with a sintered construct defining a fracture generated using the apparatus of FIG. 1.

In one aspect, in forming the fractured sintered construct 100 of FIG. 2 by utilizing the assembly of FIG. 1, and as previously mentioned, the metal sheet 30 is suspended in the tube 10 and surrounded by glass beads 20. The metal sheet 30 may be suspended in tube 10 in any of several manners. By way of example, tube 10 may be partially filled with well-mixed beads 20, and then sheet 30 may be laid over the beads already in the tube. Another manner of suspending the sheet 30 in the tube 10 is to extend the sheet 30 beyond the length of the tube and utilizing a clamp and a stand (not shown) to clamp the sheet 30 in place. Another manner of suspending the sheet 30 in the tube 10 is to attach extremely thin wires to ends of the sheet 30 and run the wires out to a clamp which holds the wires in tension. Other manners of suspending the sheet 30 may be used. With the sheet 30 is suspended in the tube 10, the beads 20 are poured into the surrounding space. Periodic vibration of the tube 10 and sheet 30 as the beads are poured into the surrounding space may aid in forming a random closed packing of the beads 20.

Figure 3:
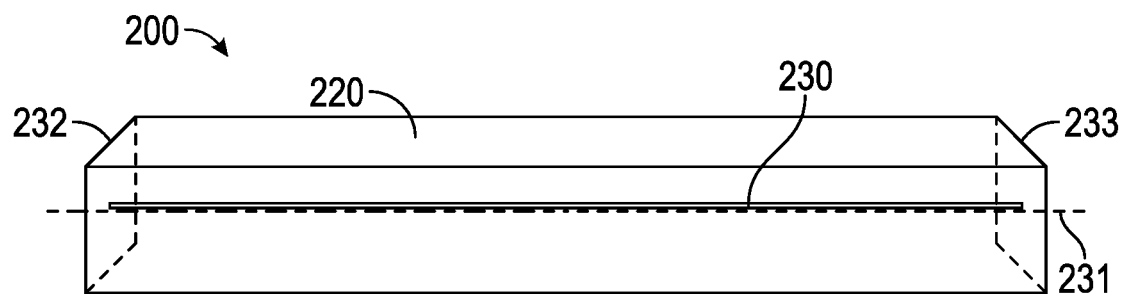
FIG. 3 is a three dimensional rendering of a physical model of an earth formation with a sintered construct that defines a channel.

Turning to FIG. 3, an elongate fractured sintered construct 200 is seen which was formed by suspending a metal wire (not shown) having a diameter of approximately 0.1 mm in a tube (e.g., in some cases the diameter of the wire is substantially smaller than the bead size), and packing glass beads around the wire, sintering the beads as previously discussed with respect to FIGS. 1 and 2, and dissolving the metal wire. The resulting construct 200 includes a sintered matrix 220 defining a channel 230. The sintered construct 200 has a longitudinal axis 231 as well as a lengthwise dimension between opposed ends 232 and 233. The channel 230 extends along the entire lengthwise dimension of the sintered construct 200 in the direction of the longitudinal axis 231. The channel 230 has a length that is at least one hundred times larger than the average pore size between the sintered beads, and at least twice the average pore size in width and height.

In one embodiment, the hollow tube 10 is rectangular in cross-section. The tube may assume any desired size. By way of example only, a tube may be 6 mm×6 mm in cross section or 12 mm×12 mm in cross section, or any other desired useful size, whether smaller or larger. The tube may be square or rectangular in cross section. The tube may also be of a desired length such as 30 mm or 70 mm, or any other desired length. In another embodiment, the hollow tube 10 is circular or oval in cross section.

The hollow tube 10 may also be made of any of many materials, provided the tube 10 will not melt during the process of sintering the beads and will not react with the solvent that is used to dissolve the metal sheet or wire. In one embodiment the hollow tube 10 is made of quartz. In another embodiment, the hollow tube is made of borosilicate glass. In another embodiment, the hollow tube is made of titanium. In one aspect, a clear (transparent or translucent) material is useful for the hollow tube 10 so that the sintered construct contained in the hollow tube is visible to the human eye when fluid is introduced to the sintered construct.

In one embodiment, the beads 20 may be made of any of many materials, provided that they can be sintered into a construct mimicking a geological formation, that they will not react with the solvent that is used to dissolve the sheet or wire and that they have a softening temperature below the softening temperature of the hollow tube. In one embodiment where the hollow tube is made from quartz, the beads 20 are made from borosilicate glass. In one embodiment where the hollow tube is made from borosilicate glass, the beads are made from soda-lime glass. In one aspect, it can be useful for the beads 20 to have dimensions of different sizes. Thus, in one embodiment, beads having diameters between 1 micron and 5000 microns are utilized, although it will be appreciated that where a large bead is utilized, numerous small beads are also utilized to ensure that the pore sizes remain small. The percentages of beads having specific diameters may be selected as desired or the selection may be random. In one embodiment, the beads with different diameter sizes are mixed before placement in the hollow tube to ensure a random distribution, and as the beads are introduced into the hollow tube 10, the hollow tube may be shaken with a shaker or by hand to ensure that the beads are well mixed. If desired, the tube 10 and sheet 30 may also be vibrated as the beads are poured in order to aid in a random packing.

In one embodiment, the sheet 30 or wire may be made of any of many materials provided that they will not melt at the sintering temperature of the hollow beads 20, and provided they can be dissolved without injuring the sintered construct. By way of example and not by way of limitation, the sheet or wire may be made of copper, zinc or tin. The sheet is typically between 100 microns and 2 millimeter thick and is at least one hundred times longer and wider than the average pore size of the sintered construct. Similarly, the wire is typically between 100 microns and one millimeter in diameter and at least one hundred times longer than the average pore size of the sintered construct.

In one embodiment, a plurality of sheets and/or wires are placed at different locations in the hollow tube 10 and have beads surrounded them prior to sintering. A sheet and a wire may be used together and displaced one from the other. The sheet(s) and/or wire(s) may be displaced from each other in one or more of the three dimensions.

Although only a few examples have been described in detail above, those skilled in the art will readily appreciate that many modifications are possible in the examples without materially departing from this subject disclosure. Thus, by way of example only, and not by way of limitation, while various embodiments describe tubes, beads, and sheets (or wires) of particular materials, other materials may be utilized provided that the tube (and sheets or wires) will not be damaged during sintering of the beads and provided that the sintered beads will not be damaged during dissolving of the sheets or wires. Also, while tubes, beads and sheets of particular sizes are described, other sizes may be utilized, provided that the desired fracture or channel is obtained. Further, while particular temperatures and heating times were described with respect to the sintering process, it will be appreciated that other temperatures and heating times could be utilized. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method of fabricating a consolidated porous media sample, the method comprising:
   assembling an assembly having an outer tube having opposed open ends and a first softening temperature, at least one sheet or wire of dissolvable material, and a plurality of beads of multiple sizes having a second softening temperature below the first softening temperature, wherein the at least one sheet or wire of dissolvable material is disposed in the outer tube with the plurality of beads packed around the at least one sheet or wire;
   sintering the plurality of beads with the at least one sheet or wire disposed therein to generate an elongate sintered construct defining pores by applying heat at the second softening temperature, wherein the elongate sintered construct has a lengthwise dimension extending between the opposed open ends of the outer tube; and
   dissolving the at least one sheet or wire to define at least one fracture or channel in the sintered construct that extends along the entire lengthwise dimension of the sintered construct that extends between the opposed open ends of the outer tube, wherein the at least one fracture or channel is configured to replicate or mimic a fracture in reservoir rock.

2. The method of claim 1, wherein the outer tube and the beads are translucent or transparent.

3. The method of claim 1, wherein the dissolving comprises soaking the sintered construct in a solvent.

4. The method of claim 3, wherein the solvent comprises nitric acid or ferric chloride.

5. The method of claim 3, further comprising flushing the sintered construct with water after the dissolving.

6. The method of claim 1, wherein the least one sheet or wire of dissolvable material is held in tension in the outer tube.

7. The method of claim 1, wherein the outer tube is formed from quartz, the beads are formed from borosilicate glass, and the at least one sheet or wire is formed from metal.

8. The method of claim 1, wherein the outer tube is rectangular in cross section.

9. The method of claim 1, wherein the at least one fracture or channel comprises a fracture having an aperture of between 100 microns and 2 millimeters.

10. The method of claim 1, wherein the sintered construct has a longitudinal axis, and the at least one fracture or channel extends in the direction of the longitudinal axis.

11. The method of claim 1, wherein the sintered construct comprises sintered beads that form a porous structure with pores of different sizes with an average pore size, and length of the at least one fracture or channel is at least one hundred times larger than the average pore size.

12. The method of claim 11, wherein the average pore size is less than 0.05 mm in diameter.

13. The method of claim 11, wherein width of the at least one fracture or channel is at least one hundred times larger than the average pore size.

14. The method of claim 11, wherein height of the at least one fracture or channel is at least twice the average pore size.

* * * * *